United States Patent
deLoache, III et al.

(10) Patent No.: US 11,471,591 B1
(45) Date of Patent: Oct. 18, 2022

(54) INTRAVENOUS (IV) BAG HANGER WITH LIGATURE-RESISTANCE

(71) Applicant: Behavioral Safety Products, LLC, Athens, GA (US)

(72) Inventors: Robert Lee deLoache, III, Watkinsville, GA (US); David Cory deLoache, Watkinsville, GA (US); Mark Mendes, Loganville, GA (US)

(73) Assignee: Behavioral Safety Products, LLC, Athens, GA (US)

( * ) Notice: Subject to any disclaimer, the term of this patent is extended or adjusted under 35 U.S.C. 154(b) by 0 days.

(21) Appl. No.: 17/513,774

(22) Filed: Oct. 28, 2021

(51) Int. Cl.
*A61M 5/14* (2006.01)
*F16B 45/00* (2006.01)
*A47G 25/06* (2006.01)

(52) U.S. Cl.
CPC ........ *A61M 5/1417* (2013.01); *A61M 5/1415* (2013.01); *A47G 25/0642* (2013.01); *A61M 2205/276* (2013.01); *F16B 45/00* (2013.01)

(58) Field of Classification Search
CPC .......... A47G 25/06542; A47G 25/0685; A47G 25/0642; A61M 2205/276; A61M 5/1414; A61M 5/1417; A61M 5/1415; F16B 45/00
USPC ......... 248/95, 685, 548, 900, 304–308, 553; 211/1.3, 100; 70/62
See application file for complete search history.

(56) References Cited

U.S. PATENT DOCUMENTS

| | | | |
|---|---|---|---|
| 2,434,009 A * | 1/1948 | Palmer | A62C 13/003 248/553 |
| 2,901,207 A * | 8/1959 | Folger | A47G 25/0642 188/204 R |
| 3,424,418 A | 1/1969 | Freedman et al. | |

(Continued)

FOREIGN PATENT DOCUMENTS

| | | |
|---|---|---|
| CN | 110882436 A | 3/2020 |
| CN | 112354041 A | 2/2021 |

(Continued)

OTHER PUBLICATIONS

GrabBarDirect; Anti-Suicide Hooks; Feb. 1, 2002; https://www.grabbarsdirect.com/Anti_Suicide_Hooks_s/77.htm (Year: 2002).*

(Continued)

*Primary Examiner* — Ingrid M Weinhold
(74) *Attorney, Agent, or Firm* — Mitch Harris, Atty at Law, LLC; Andrew M. Harris

(57) ABSTRACT

A ligature-resistant bag hanger for supporting an intravenous (IV) bag prevents formation of ligatures over an IV pole and on the bag support hooks. Internal components of the ligature-resistant IV bag hanger are enclosed in a housing. The internal components of the ligature-resistant bag hanger include one or more bag support hooks that have an extension portion extending from an interior of the housing and that are rotatable around an axle located within the housing. In a reset position, the bag support hook(s) support(s) an intravenous bag in a saddle portion of the hook up to a threshold weight limit. In a triggered position, initiated by a downward force in excess of the threshold weight limit rotating the hook downward, the hook rotates so that an attempted ligature formed above the saddle portion of the hook is released by retraction of the saddle portion of the within the housing.

20 Claims, 6 Drawing Sheets

(56) References Cited

U.S. PATENT DOCUMENTS

| | | | |
|---|---|---|---|
| 3,666,224 A * | 5/1972 | Domanico | A62C 13/78 248/553 |
| 3,847,336 A * | 11/1974 | Morris | A47G 25/0642 74/584 |
| 3,900,180 A * | 8/1975 | McPhee | A47K 10/12 248/309.2 |
| 3,957,241 A | 5/1976 | Morris et al. | |
| 4,221,354 A | 9/1980 | Kempers | |
| 4,537,434 A | 8/1985 | Piercy | |
| 4,695,025 A | 9/1987 | Vaughan | |
| 4,807,837 A * | 2/1989 | Gawlik | F16M 11/22 211/196 |
| 7,131,616 B2 * | 11/2006 | Livingstone | A47G 25/0642 248/304 |
| 8,011,633 B2 | 9/2011 | Huang | |
| 8,584,494 B2 | 11/2013 | Salvatore et al. | |
| D731,291 S | 6/2015 | Boeltl | |
| D736,061 S | 8/2015 | Boeltl | |
| 9,297,154 B2 | 3/2016 | deLoache, III et al. | |
| 9,301,658 B1 | 4/2016 | Boeltl | |
| 9,669,155 B2 | 6/2017 | Chepurney | |
| D792,955 S | 7/2017 | deLoache, III | |
| 9,938,704 B2 | 4/2018 | deLoache, III | |
| 9,950,108 B2 | 4/2018 | Alkire et al. | |
| 10,220,790 B2 | 3/2019 | Mozurkewich et al. | |
| 10,610,037 B1 | 4/2020 | deLoache, III et al. | |
| 2006/0071136 A1 * | 4/2006 | Livingstone | A47G 25/0642 248/308 |
| 2006/0071137 A1 * | 4/2006 | Livingstone | F16B 45/00 248/308 |
| 2011/0035910 A1 | 2/2011 | Wu | |
| 2018/0135286 A1 | 5/2018 | deLoache, III | |

FOREIGN PATENT DOCUMENTS

| | | |
|---|---|---|
| GB | 2504710 B | 9/2014 |
| IN | 201641041424 A | 6/2018 |

OTHER PUBLICATIONS

BobBarker, "Lifeline Safety Hook", downloaded from https://www.bobbarker.com/lifeline-antisuicide-hook.html on Aug. 8, 2018, 2 pages (pp. 1-2 in pdf).

Cape Cod Systems, "Single Hook Panel, CCSW1830-SLPT", downloaded from https://www.capecodsystemscompany.com/store/-ccsw1830-slpt,product.asp on Aug. 8, 2018, 4 pages (pp. 1-4 in pdf).

Whitehall Manufacturing, "Ligature Resistant Adjustable Auto-Release Clothes Hook", downloaded from https://www.whitehallmfg.com/product.aspx?productid=1019 on Oct. 22, 2018, 2 pages (pp. 1-2 in pdf).

Cape Cod Systems, "Kingsway Anti Ligature Dual Coat Hook Rack, CCS_KG177", downloaded from https://www.capecodsystemscompany.com/store/ccs_kg177,Product.asp on Oct. 22, 2018, 4 pages (pp. 1-4 in pdf).

Cape Cod Systems, "ASi, Clothes Hook, Square—Chase Mount, CCS_ASi_122", downloaded from https://www.capecodsystemscompany.com/store/ccs_asi_122_squareclotheshook,Product.asp.

Cape Cod Systems, "ASi, Clothes Hook, Chase Mount, CCS_ASI_121_ClothesHook", downloaded from https://www.capecodsystemscompany.com/store/ccs_asi_121_clotheshook,Product.asp.

Cape Cod Systems, "A&J Washroom Security Hook For Chase Walls, CCSA18", downloaded from https://www.capecodsystemscompany.com/store/security-15-exposed-mount-hook,Product.asp on Oct. 22, 2018, 5 pages (pp. 1-5 in pdf).

* cited by examiner

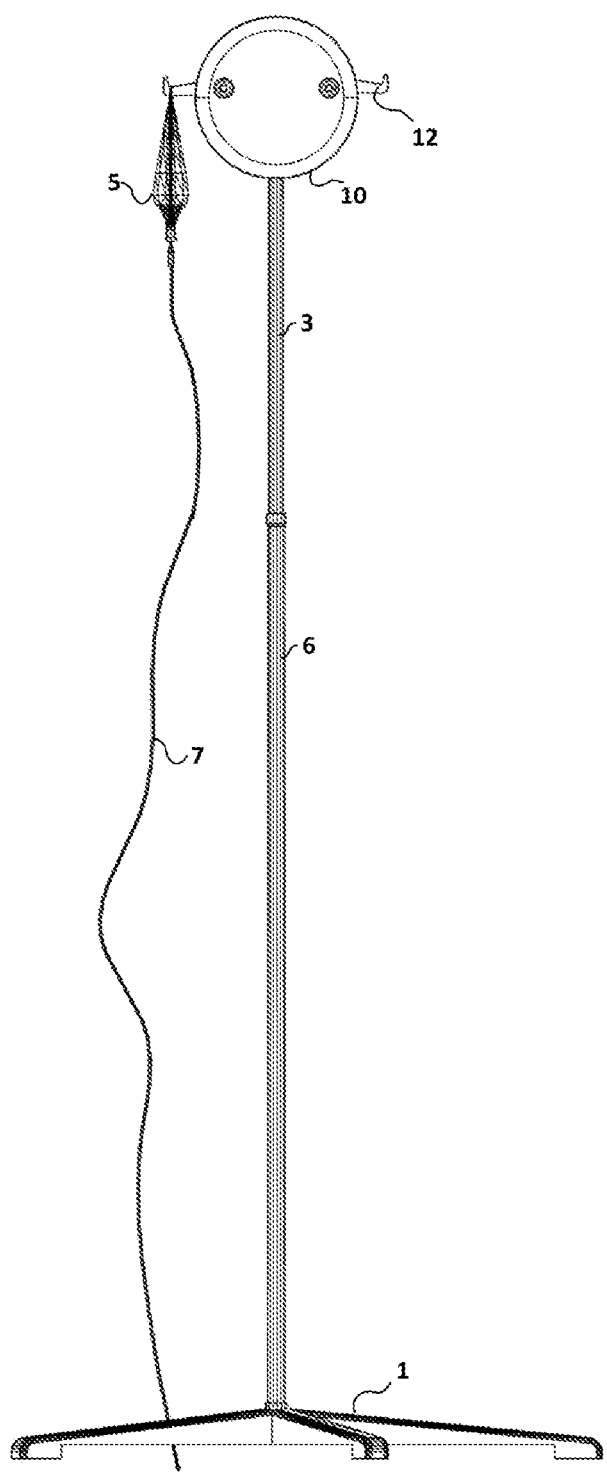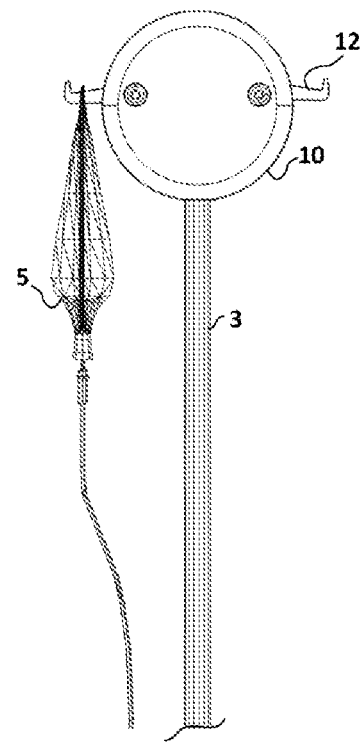
Fig. 1A
Fig. 1B

INTRAVENOUS (IV) BAG HANGER WITH LIGATURE-RESISTANCE

BACKGROUND OF THE INVENTION

1. Field of the Invention

The present invention relates generally to ligature-resistant devices and above-the-patient hangers for intravenous bags and other suspended lines in a medical environment.

2. Description of the Related Art

Ligature-resistant design is a requirement in many institutional locations. In particular, in rooms where persons may be left unattended and where there is a risk that fixtures may be used as a support to tie a ligature, such as a belt, rope or a cloth, a way to ensure that the fixtures cannot be used in such a manner is desirable. In general, ligature-resistant design is an issue that exists any height above the floor, since objects above the floor can be used to support a ligature, even if one is not attachable.

Typical intravenous (IV) bag hangers are either fixed-mounted or provided on a bag stand, which may have a portable base, a mounted base, or be configured for rolling or other movement. Even though the bag hanger may not provide a stable mounted location, they can be used to form ligatures downward and typically provide a substantial amount of height above the ground to which a ligature can be attached.

Therefore, it would be desirable to provide an IV bag hanger and/or holder for other suspended lines that prevents ligature formation and/or support of such ligatures.

SUMMARY OF THE INVENTION

The above objectives, among others, are achieved in a ligature-resistant intravenous (IV) bag hanger and a method of supporting an IV bag above a patient.

The ligature-resistant bag hanger includes a housing for holding internal components of the ligature-resistant support, and internal components of the ligature-resistant bag hanger including at least one bag support hook that has an extension portion extending from an interior of the housing and is rotatable around an axle located within the housing. The at least one bag support hook, in a reset position, provides support of the intravenous bag in a saddle portion of the at least one bag support hook up to a threshold weight limit. The at least one bag support hook, in a triggered position initiated by a downward force in excess of the threshold weight limit rotating the hook downward, rotates to a position in which an attempted ligature formed above the saddle portion of the at least one bag support hook is released by retraction of the saddle portion of the at least one bag support hook within the housing.

The summary above is provided for brief explanation and does not restrict the scope of the claims. The description below sets forth example embodiments according to this disclosure. Further embodiments and implementations will be apparent to those having ordinary skill in the art. Persons having ordinary skill in the art will recognize that various equivalent techniques may be applied in lieu of, or in conjunction with, the embodiments discussed below, and all such equivalents are encompassed by the present disclosure.

BRIEF DESCRIPTION OF THE DRAWINGS

FIG. 1A is a perspective view of an installation of an example ligature-resistant intravenous (IV) bag hanger 10 mounted atop a pole 3 of an IV bag stand, in accordance with an embodiment of the disclosure.

FIG. 1B is an enlarged front view of a portion of the installation of FIG. 1A.

DETAILED DESCRIPTION OF ILLUSTRATIVE EMBODIMENT

Figure 2A:
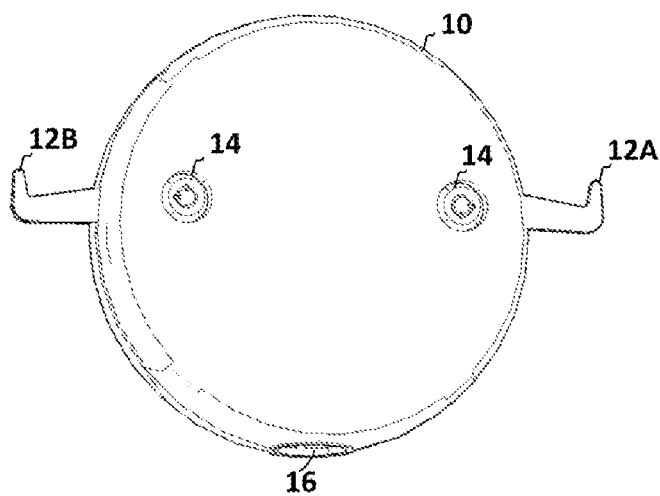
FIG. 2A, FIG. 2B and FIG. 2C are a front perspective view, a bottom right perspective view and a front right perspective view, respectively, of ligature-resistant IV bag hanger 10 of FIG. 1A and FIG. 1B.

The present disclosure illustrates intravenous (IV) bag hangers provide ligature-resistance over the bag hanger and that releases a ligature supporting a weight above a threshold weight over one or more bag support hooks. The internal components of the ligature-resistant support are enclosed in a housing. The internal components of the ligature-resistant bag hanger include one or more bag support hooks that have an extension portion extending from an interior of the housing and that are rotatable around an axle located within the housing. In a reset position, the bag support hook(s) provides support of an intravenous bag in a saddle portion of the hook up to a threshold weight limit. In a triggered position, initiated by a downward force in excess of the threshold weight limit rotating the hook downward, the hook rotates so that an attempted ligature formed above the saddle portion of the hook is released by retraction of the saddle portion of the within the housing.

Referring now to FIG. 1A, a perspective view of an installation of an example ligature-resistant intravenous (IV) bag hanger 10 atop a pole 3 of an IV bag stand 6 is shown, in accordance with an embodiment of the disclosure. IV bag stand 6 includes pole 3 affixed to a base 1 that supports stand 6 in a vertical orientation, and which is illustrated as a fixed base that is lifted for transport, but which may include rollers or slides, or the like. IV bag hanger 10 is approximately 8" in diameter and has an aperture at a bottom of the housing of IV bag hanger 10 for accepting pole 3. Adapters for accommodating various sizes of poles can be used with IV bag hanger 10 by insertion within the aperture as will be further described below. IV bag hanger 10 has a curved upper surface, both along the width of IV bag hanger 10 as illustrated, but also along the depth, so that any attempt to form a ligature above IV bag hanger 10, will result in the ligature slipping off of the housing of IV bag hanger 10. IV bag hanger 10 further incorporates features associated with bag support hooks 12 as described in detail below. Bag support hooks 12 will release when a weight greater than a threshold weight, e.g., 5 lbs on one of bag support hooks 12 is exceeded. Since the typical weight of an IV bag 5 is 1 lb, plus any weight of the connected associated line 7 and any slight pulling by a patient or staff, is likely not to exceed 5 lbs. However, the weight needed to form a ligature on bag support hooks 12 will exceed 5 lbs, such a threshold weight should be sufficient to ensure safety. FIG. 1B is an enlarged front view of a portion of the installation of FIG. 1A, showing details of hooks 12 lying in a substantially horizontal position when unloaded by a weight greater than the threshold weight.

Figure 2B:
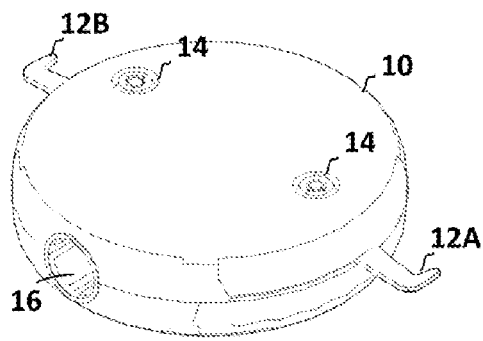
Figure 2C:
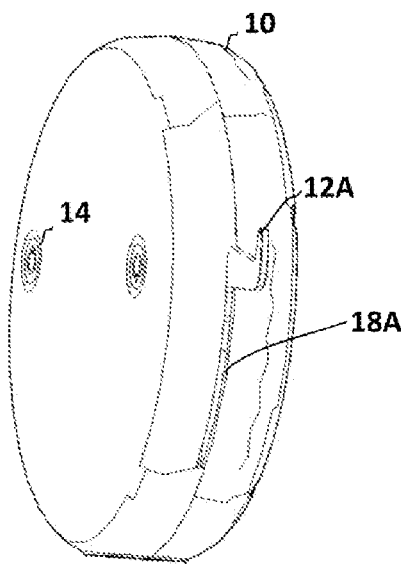

Referring now to FIG. 2A, FIG. 2B and FIG. 2C, a front perspective view, a bottom right perspective view and a front right perspective view, respectively, of example ligature-resistant IV bag hanger 10 of FIG. 1A and FIG. 1B, are shown. At a front face of ligature-resistant IV bag hanger 10, a pair of keylocks are accessible that are used to individually reset bag support hooks 12A,12B after they are triggered by a weight in excess of the threshold weight. Slots 18A are provided on either side of ligature-resistant IV bag hanger 10 so that bag support hooks 12A,12B can extend from inside of the housing of ligature-resistant IV bag hanger 10 in the reset position and so that at least the saddle portions of bag support hooks 12A,12B that might otherwise be used to support a ligature can retract within the housing of ligature-resistant IV bag hanger 10 as will be described below. A position of pole aperture 16 is shown. While pole-mounting is a feature of the illustrated embodiment, it should be understood that pole aperture 16 may be omitted in embodiments that are intended for mounting on other structures, such as a wall or fastened to another, portable structure, in a room.

Figure 3A:
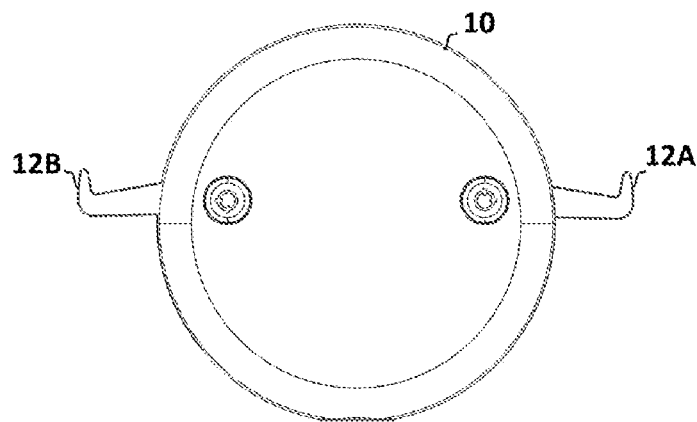
FIG. 3A, FIG. 3B and FIG. 3C are front views of ligature-resistant IV bag hanger 10 of FIG. 1A an FIG. 1B in various states of operation.
Figure 3B:
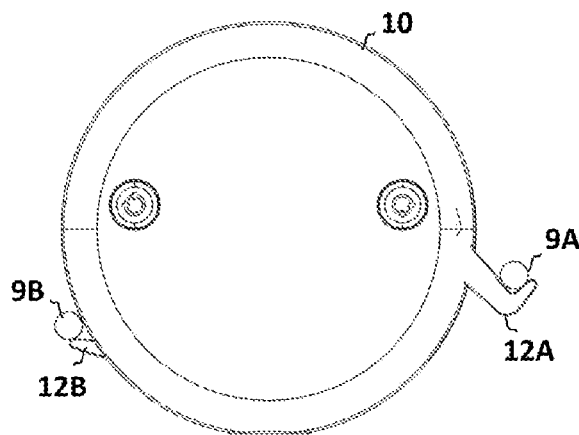
Figure 3C:
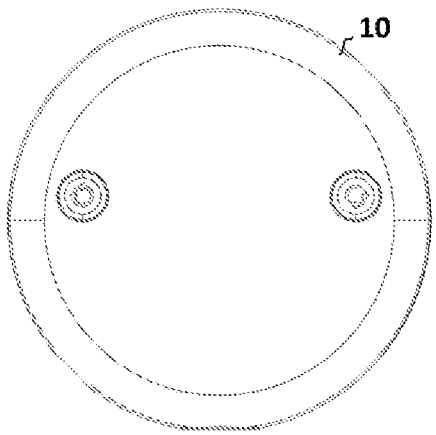

Referring now to FIG. 3A, FIG. 3B and FIG. 3C front views of example ligature-resistant IV bag hanger 10 of FIG. 1A and FIG. 1B in various states of operation are shown. FIG. 2A shows both a left bag support hook 12B and a right bag support hook 12A in a reset position, which is the position in which both left bag support hook 12B and a right bag support hook 12A will remain until a weight greater than the threshold weight is applied to one of both of left bag support hook 12B and right bag support hook 12A. FIG. 3B illustrates positions that bag support hooks 12A and 12B will move through if weighed down with a load weight greater than the threshold weight. Bag support hook 12A is moving downward due to a weight applied to a cord 9A that exceeded the threshold weight, releasing bag support hook 12A to swing down freely, bag support hook 12B is illustrated in a further position in which the saddle of bag support hook 12B has retracted to a point at which the saddle at the junction of the hook tip and the remainder of bag support hook 12B has moved inside of the housing of IV bag hanger 10, at which point a cord 9B is released from bag support hook 12B. FIG. 3C illustrates an ultimate position of bag support hooks 12A, 12B, after they experience a load greater than the threshold weight, and in which bag support hooks 12A, 12B are retracted fully within the housing of ligature-resistant IV bag hanger 10. While, in the illustrated embodiment, bag support hooks 12A, 12B move independently and, unless both of bag support hooks 12A, 12B are loaded in excess of the threshold weight, only one of bag support hooks 12A, 12B will be triggered when loaded with a weight in excess of the threshold weight, in other embodiments, either of bag support hooks 12A, 12B may trigger a release of both bag support hooks 12A, 12B when loaded in excess of the threshold weight.

Figure 4:
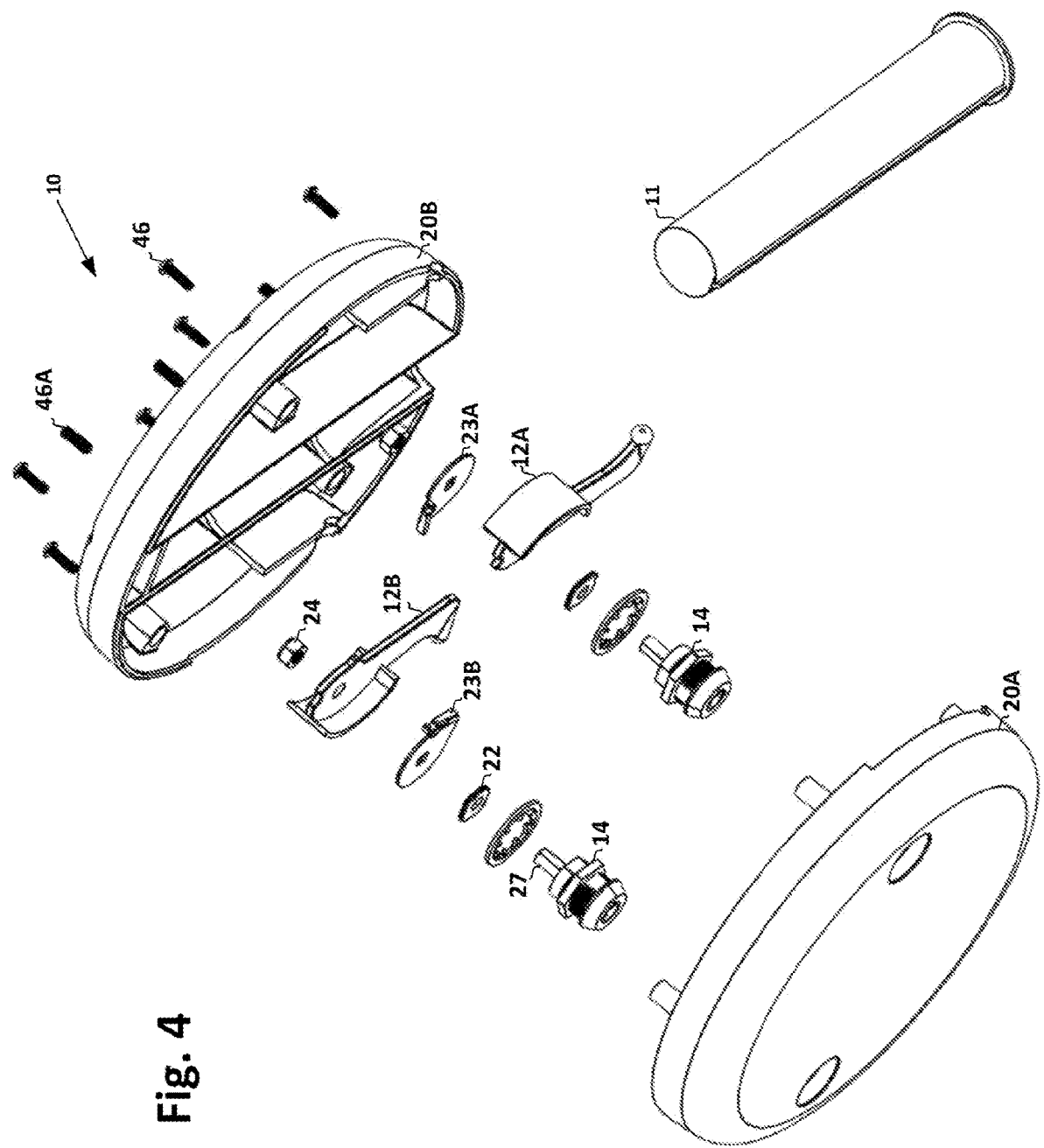
FIG. 4 is an exploded view of an example ligature-resistant IV bag hanger 10, in accordance with an embodiment of the disclosure.

Referring now to FIG. 4, an exploded view of example ligature-resistant IV bag hanger 10 is shown, in accordance with an embodiment of the disclosure. As illustrated, the housing of example ligature-resistant IV bag hanger 10 is formed by a front housing portion 20A and a rear housing portion 20B that enclose internal components of ligature-resistant IV bag hanger 10, except for the extensions of bag support hooks 12A, 12B, when bag support hooks 12A, 12B are in the reset position, and the front faces of keylocks 14 that are exposed through apertures formed through front housing portion 20A that receive the bodies of keylocks 14, which are fastened into the apertures by retaining nuts. Keylocks 14 provide rotating cylinders 27 that serve as axles for rotation of bag support hooks 12A, 12B, which are retained to keylocks 14 with an assembly including, for each of keylocks 14 and their corresponding bag support hooks 12A, 12B, a star washer, a spacer washer 22, a hook release spring 23A,23B and a nut 24. Hook release springs 23A,23B are mounted on different sides of bag support hooks 12A, 12B, which permits use of the same design for hook release springs 23A,23B, while providing for the opposite direction of released rotation of bag support hooks 12A, 12B. A plurality of machine screws 46 retains rear housing portion 20B to front housing portion 20A, completing the assembly of example ligature-resistant IV bag hanger 10. Set screws 46A are inserted through inserts in rear housing portion 20B to secure example ligature-resistant IV bag hanger 10 to a pole. An insert for smaller pole sizes may be provided 10 to adapt example ligature-resistant IV bag hanger 10 to smaller poles. For example, the diameter of aperture 16 may be 1", allowing mounting on 1" diameter poles, with adapters provided for ¾" and ½" poles that may be inserted in aperture, with the adapters and example ligature-resistant IV bag hanger 10 secured by set screws 46A.

Figure 5A:
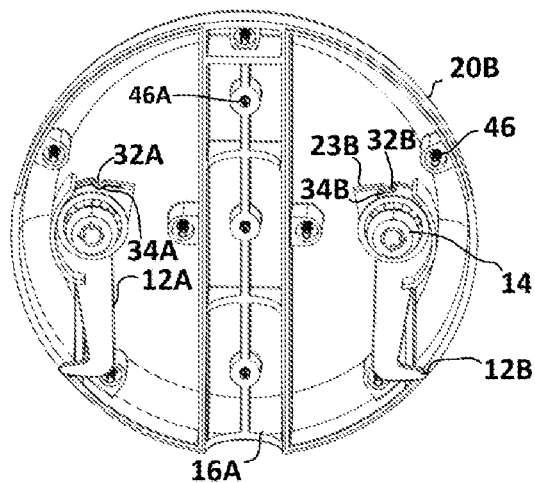
FIG. 5A is an internal front perspective view of a rear housing portion 20B, showing internal features of example ligature-resistant IV bag hanger 10 with a front housing portion 20A removed
Figure 5B:
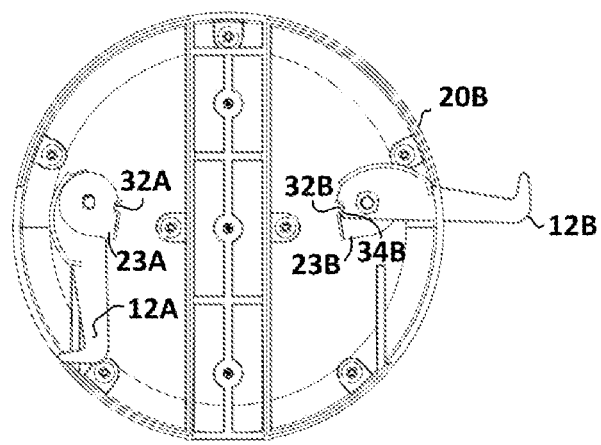
FIG. 5B is an internal front view of rear housing portion 20B with front housing portion 20A removed along with locks 14 and other components, to further illustrate operation of example ligature-resistant IV bag hanger 10.

Referring now to FIG. 5A and to FIG. 5B, an internal front perspective view, and a front view, respectively, of a rear housing portion 20B and internal features of example ligature-resistant IV bag hanger 10 is shown, with a front housing portion 20A removed. In FIG. 5A, bag support hooks 12A, 12B are in a partially reset position after being triggered and after a key has been inserted in keylocks 14 and the key turned (clockwise for bag support hook 12A and counter-clockwise for bag support hook 12B) to restore the position of indentations 34A, 34B formed on the perimeter of an end of the extension of bag support hooks 12A, 12B opposite the end of bag support hooks 12A, 12B that forms their saddle portions. Once one of indentations 34A, 34B has been engaged with the corresponding leaf 32A, 32B of hook release springs 23A, 23B, the key is turned counter-clockwise to extend an extension portion of bag support hook 12B as illustrated in FIG. 5B. Since hook release springs 23A, 23B turn with the rotation of keylocks 14, due to their central aperture having a shape that fits one or more flats formed on the shaft of keylocks 14, but bag support hooks 12A, 12B have circular central apertures, bag support hooks 12A, 12B rotate freely once a spring leaf 32A, 32B is released from the corresponding indentation 34A, 34B. Release of the bag support hooks 12A, 12B is due to the corresponding one of bag support hooks 12A, 12B being triggered by a weight in excess of the threshold weight, which is determined by the force required to displace a spring leaf 32A, 32B from the corresponding indentation 34A, 34B sufficiently to allow bag support hooks 12A, 12B to rotate the indentation 34A, 34B past spring leaf 32A, 32B to free bag support hooks 12A, 12B.

Bag support hook 12A in the illustration of FIG. 5B is in the triggered position, so that bag hanger hook 12A freely rotates downward, while hook release spring 23A remains in position with spring leaf 32A released from bag support hook 12A. As described above, to reset bag support hook 12A the corresponding one of locks 14 is rotated counterclockwise, which rotates hook release spring 23A counterclockwise until spring leaf 32A is engaged with indentation 34A of bag support hook 12A, which restores bag support hook to the partially-reset position shown in FIG. 5A. To restore bag support hook 12A to the reset position of bag support hook 12B in FIG. 5B, the key is rotated clockwise to extend bag support hook 12A upward and outward.

Figure 5C:
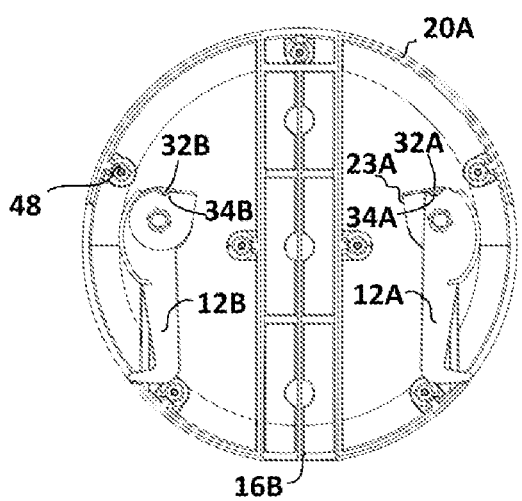
FIG. 5C is an internal rear view of a front housing portion 20A, showing internal features of example ligature-resistant IV bag hanger 10 with a rear housing portion 20B removed.

FIG. 5C is an internal rear view of a front housing portion 20A, showing internal features of example ligature-resistant IV bag hanger 10 with a rear housing portion 20B removed. The position of bag support hooks 12A, 12B is the partially-reset position of FIG. 5A, in which spring leaves 32A, 32B are captured within indentations 34A, 34B of bag support hooks 12A, 12B.

Figure 6:
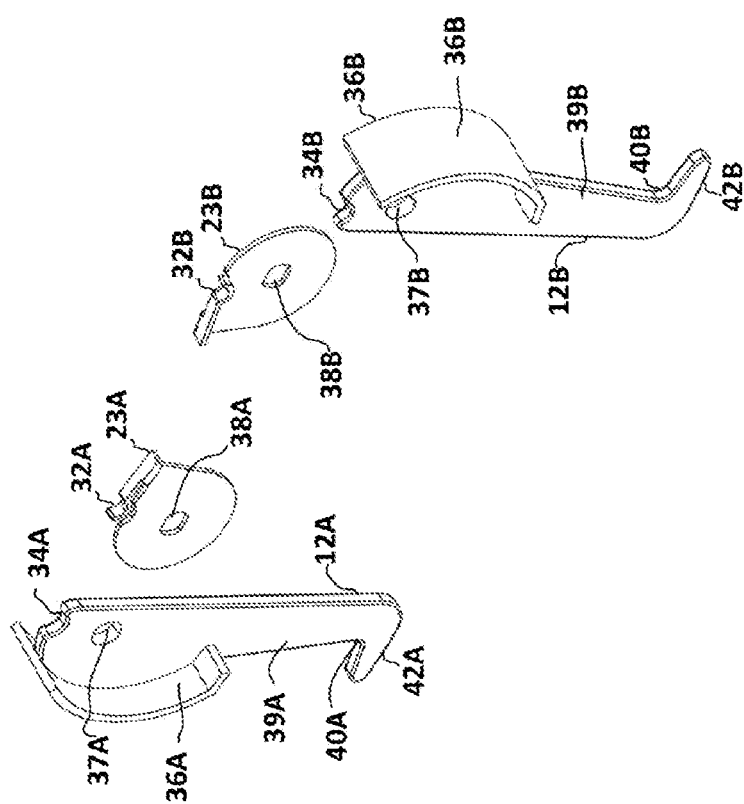
FIG. 6 is a detailed perspective view of left and right bag support hooks 12A, 12B and left and right hook release springs 43A, 43B of example ligature-resistant bag hanger 10.

Referring now to FIG. 6, a detailed perspective view of left and right bag support hooks 12A, 12B and left and right hook release springs 23A, 23B of example ligature-resistant bag hanger 10, is shown. Bag support hooks 12A, 12B include extension portions 39A, 39B that extend through slots (e.g., slot 18A as shown in FIG. 2C) in the housing of example ligature-resistant IV bag hanger 10, when bag support hooks 12A, 12B are in the reset position. Bag support hooks 12A, 12B also include shields 36A, 36B that, when bag support hooks 12A, 12B are in the reset position, blocks entry of a cord, etc., that might be used to form a ligature, and also prevents intrusion of dust or debris. Circular-profile apertures 37A, 37B receive the shaft of a corresponding keylock, which serves as an axle inside the housing, around which bag support hooks 12A, 12B rotate when release or while being reset. Bag support hooks 12A, 12B also include hook tips 42A, 42B that form a saddle portion 40A, 40B that supports an IV bag or other objects having up to the threshold weight. The location of indentations 34A, 34B is shown, along with the details of hook release springs 23A, 23B, their spring leaves 32A, 32B and flatted central apertures 38A, 38B that turn with the shafts of keylocks 14.

In summary, this disclosure shows and describes ligature-resistant bag hangers for supporting intravenous bags. The ligature-resistant bag hangers include a housing for holding internal components of the ligature-resistant bag hanger, and internal components of the ligature-resistant bag hanger including at least one bag support hook having an extension portion extending from an interior of the housing and rotatable around an axle located within the housing. The at least one bag support hook, in a reset position, provides support of the intravenous bag in a saddle portion of the at least one bag support hook up to a threshold weight limit, and in a triggered position initiated by a downward force in excess of the threshold weight limit rotating the bag support hook downward, the at least one bag hook rotates to a position in which an attempted ligature formed above the saddle portion of the at least one bag support hook is released by retraction of the saddle portion of the at least one bag support hook within the housing.

In some example embodiments, the ligature-resistant bag hanger may further include at least one keyed security device accessible at an exterior surface of the housing, and the saddle portion of the at least one bag support hook may be retained within the housing in the triggered position until released by activation of the keyed security device. In some example embodiments, the at least one keyed security device may be a lock having rotor that is rotatable when turned by a key, and the rotor may be mechanically coupled to the extension portion of the at least one bag support hook to rotate the at least one bag support hook to the reset position. In some example embodiments, the housing of the ligature-resistant bag holder may include a rear housing portion having a substantially circular first external profile along at least a top portion of the first external profile in a plane of a front edge of the rear housing portion, and a front housing portion having a second external profile matching the substantially circular first external profile of the rear housing portion along a back edge of the front housing portion. The front housing portion and the rear housing portion, when the front edge of the rear housing portion and the back edge of the front housing portion are joined, may form a continuous surface having a third curved external profile in a direction perpendicular to the first external profile and the second external profile along the at least a top portion of the first external profile, whereby formation of a ligature around a top edge of the housing around the first external profile or the third external profile may be prevented. The rear housing portion and the front housing portion may define at least one slot extending along the first external profile and the second external profile at a junction between the rear housing portion and the front housing portion, through which the extension portion of the at least one bag support hook extends when the at least one bag support hook is in the reset position and through which the at least one bag support hook may retract when the at least one bag support hook is triggered. In some example embodiments, at least one of the rear housing portion and the front housing portion may define a circular aperture at a bottom edge of the housing, for accepting a pole of an intravenous bag stand.

In some example embodiments, the ligature-resistant bag hanger the at least one bag support hook may include two bag support hooks disposed at opposite lateral edges of the housing. In some example embodiments, the internal components of the ligature-resistant bag hanger may include at least one hook release spring that restricts rotation of the extension portion of the at least one bag support hook when the saddle portion of the at least one bag support hook is loaded with a weight less than or equal to the threshold weight limit, and the at least one hook release spring may release the extension portion of the at least one bag support hook to rotate freely once the at least one bag support hook is loaded with a weight greater than the threshold weight limit. In some example embodiments, the at least one hook release spring may be a disc defining a central hole and having a spring leaf disposed along a portion of circumference thereof and extending therefrom to a shaped end of the spring leaf. The at least one hook release spring leaf may be mounted around the at least one axle with the axle extending through the central hole. The at least one bag support hook may have an indentation formed around an edge of the extension portion for receiving the shaped end of the spring leaf to restrict rotation of the extension portion of the at least one bag support hook. A rotational force may cause the indentation to move the spring leaf, so that once the at least one bag support hook is loaded with a weight greater than the threshold weight limit, the shaped end of the spring leaf is released from the indentation. In some example embodiments, the at least one hook release spring may be prevented from rotating with the extension portion of the at least one bag support hook by the at least one keyed security device when the at least one bag support hook is in the reset position. The at least one hook release spring may rotate with the extension portion of the at least one bag support hook when the shaped end of the spring leaf is released from the indentation, so that the at least one bag support hook cannot be rotated to re-engage the shaped end of the spring leaf with the indentation without activating the keyed security device. In some example embodiments the rotor of a keyed security device lock may be mechanically coupled to the extension portion of the at least one bag support hook to rotate the at least one bag support hook and the at least one hook release spring to the reset position.

It should be understood, especially by those having ordinary skill in the art with the benefit of this disclosure, that the various operations described herein, particularly in connection with the figures, may be implemented by other components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense. Similarly, although this disclosure makes reference to specific embodiments, certain modifications and changes may be made to those embodiments without departing from the scope and coverage of this disclosure. Moreover, any benefits, advantages, or solutions to problems that are described herein with regard to specific embodiments are not intended to be construed as a critical, required, or essential feature or element.

While the disclosure has shown and described particular embodiments of the techniques disclosed herein, it will be understood by those skilled in the art that the foregoing and other changes in form, and details may be made therein without departing from the spirit and scope of the disclosure.

What is claimed is:

1. A bag hanger for supporting an intravenous (IV) bag, comprising:
    a housing for holding internal components of the bag hanger; and
    internal components of the bag hanger including at least one bag support hook having an extension portion extending from an interior of the housing and rotatable around an axle located within the housing, wherein the at least one bag support hook, in a reset position, provides support of the intravenous bag in a saddle portion of the at least one bag support hook up to a threshold weight limit, wherein the at least one bag support hook, in a triggered position initiated by a downward force in excess of the threshold weight limit rotating the bag support hook downward, rotates to a position in which the saddle portion of the at least one bag support hook is retracted within the housing; and wherein the internal components of the bag hanger include at least one hook release spring that restricts rotation of the extension portion of the at least one bag support hook when the saddle portion of the at least one bag support hook is loaded with a weight less than or equal to the threshold weight limit, and that releases the extension portion of the at least one bag support hook to rotate freely once the at least one bag support hook is loaded with a weight greater than the threshold weight limit.

2. The bag hanger of claim 1, further comprising at least one keyed security device accessible at an exterior surface of the housing, wherein the saddle portion of the at least one bag support hook is rotatable to the reset position by activation of the keyed security device.

3. The bag hanger of claim 2, wherein the at least one keyed security device is a lock having a rotor that is rotatable when turned by a key, wherein the rotor is mechanically coupled to the at least one hook release spring to rotate the at least one hook release spring to engage with the at least one bag support hook and rotate the at least one bag support hook to the reset position.

4. The bag hanger of claim 1, wherein the housing comprises:
    a rear housing portion having a substantially circular first external profile along at least a top portion of the first external profile in a plane of a front edge of the rear housing portion; and
    a front housing portion having a second external profile matching the substantially circular first external profile of the rear housing portion along a back edge of the front housing portion, and wherein the front housing portion and the rear housing portion, when the front edge of the rear housing portion and the back edge of the front housing portion are joined, form a continuous surface having a third curved external profile in a direction perpendicular to the first external profile and the second external profile along the at least a top portion of the first external profile, whereby formation of a ligature around a top edge of the housing around the first external profile or the third external profile is prevented, and wherein the rear housing portion and the front housing portion define at least one slot extending along the first external profile and the second external profile at a junction between the rear housing portion and the front housing portion, through which the extension portion of the at least one bag support hook extends when the at least one bag support hook is in the reset position and through which the at least one bag support hook retracts when the at least one bag support hook is triggered.

5. The bag hanger of claim 4, wherein at least one of the rear housing portion and the front housing portion define a circular aperture at a bottom edge of the housing, for accepting a pole of an intravenous bag stand.

6. The bag hanger of claim 1, wherein the at least one bag support hook comprises two bag support hooks disposed at opposite sides of the housing.

7. The bag hanger of claim 1, wherein the at least one hook release spring is a disc defining a central hole and having a spring leaf disposed along a portion of circumference thereof and extending therefrom to a shaped end of the spring leaf, wherein the at least one hook release spring is mounted around the at least one axle with the axle extending through the central hole, wherein the at least one bag support hook has an indentation formed around an edge of the extension portion for receiving the shaped end of the spring leaf to restrict rotation of the extension portion of the at least one bag support hook, wherein a rotational force causes the indentation to move the spring leaf, so that once the at least one bag support hook is loaded with a weight greater than the threshold weight limit, the shaped end of the spring leaf is released from the indentation.

8. The bag hanger of claim 7, further comprising at least one keyed security device accessible at an exterior surface of the housing, wherein the saddle portion of the at least one bag support hook is rotatable to the reset position by activation of the keyed security device, wherein the at least one hook release spring is prevented from rotating with the extension portion of the at least one bag support hook by the at least one keyed security device when the at least one bag support hook is in the reset position.

9. The bag hanger of claim 8, wherein the at least one keyed security device is a lock having a rotor that is rotatable when turned by a key, wherein the rotor is mechanically coupled to the at least one hook release spring to rotate the at least one hook release spring to engage with the at least one bag support hook and rotate the at least one bag support hook to the reset position.

10. A method of supporting an intravenous (IV) bag while preventing formation of a ligature, the method comprising:
mounting a housing of a bag hanger above a patient; and
hanging an intravenous bag from a saddle portion of a bag support hook of the bag hanger when the bag support hook is in a reset position, wherein the bag support hook has an extension portion extending from an interior of the housing and that is rotatable around an axle located within the housing, and supports the intravenous bag up to a threshold weight limit; and
initiating a triggered position of the bag support hook by applying a downward force on the saddle portion of the bag support hook in excess of the threshold weight limit, so that the bag support hook rotates downward to a position in which the bag support hook is released by retraction of the saddle portion of the bag support hook within the housing, wherein the initiating of the triggered position of the bag support hook comprises releasing the extension of the bag support hook from a hook release spring of the bag hanger that restricts rotation of the extension portion of the bag support hook when the saddle portion of the bag support hook is loaded with a weight less than or equal to the threshold weight limit, wherein the releasing of the extension of the bag support hook releases the extension portion of the bag support hook to rotate freely once the bag support hook is loaded with a weight greater than the threshold weight limit.

11. The method of claim 10, further comprising activating a keyed security device of the bag hanger that is accessible at an exterior surface of the housing to rotate the bag support hook to the reset position, by activation of the keyed security device.

12. The method of claim 11, wherein the keyed security device is a lock having a rotor that is rotatable by turning a key within the lock, and wherein the rotor is mechanically coupled to the hook release spring to rotate the hook release spring to engage with the bag support hook and rotate the bag support hook to the reset position, by rotating the rotor by turning the key in the lock.

13. The method of claim 10, further comprising preventing formation of a ligature around a top edge of the housing and around sides of the housing by providing the housing having a rear housing portion with a substantially circular first external profile along at least a top portion of the first external profile in a plane of a front edge of the rear housing portion and a front housing portion having a second external profile matching the substantially circular first external profile of the rear housing portion along a back edge of the front housing portion, wherein the front housing portion and the rear housing portion, when the front edge of the rear housing portion and the back edge of the front housing portion are joined, form a continuous surface having a third curved external profile in a direction perpendicular to the first external profile and the second external profile along the at least a top portion of the first external profile, whereby securing a ligature around the first external profile or the third external profile is prevented, and wherein the rear housing portion and the front housing portion define a slot extending along the first external profile and the second external profile at a junction between the rear housing portion and the front housing portion, through which the extension portion of the bag support hook extends when the bag support hook is in the reset position and through which the bag support hook retracts when the bag support hook rotates to the triggered position.

14. The method of claim 13, further comprising inserting a pole of an intravenous bag stand into an aperture at a bottom end of the housing, wherein at least one of the rear housing portion and the front housing portion define the circular aperture at the bottom end of the housing.

15. The method of claim 10, wherein the bag support hook is a first bag support hook, and wherein the method further comprises providing a second bag support hook disposed at a side of the housing opposite the first bag support hook.

16. The method of claim 9, wherein the hook release spring is a disc defining a central hole and having a spring leaf disposed along a portion of circumference thereof and extending therefrom to a shaped end of the spring leaf, wherein the hook release spring is mounted around the axle with the axle extending through the central hole, wherein the bag support hook has an indentation formed around an edge of the extension portion for receiving the shaped end of the spring leaf to restrict rotation of the extension portion of the bag support hook, and wherein the releasing causes the indentation to move the spring leaf, so that once the bag support hook is loaded with a weight greater than the threshold weight limit, the shaped end of the spring leaf is released from the indentation.

17. The method of claim 16, further comprising activating a keyed security device accessible at an exterior surface of the housing to release the saddle portion of the bag support hook from the triggered position and restored to the reset position, wherein the saddle portion of the bag support hook is rotatable to the reset position when the keyed security device is activated, wherein the hook release spring is prevented from rotating with the extension portion of the bag support hook by the keyed security device when the bag support hook is in the reset position.

18. The bag hanger of claim 17, wherein the keyed security device is a lock having a rotor that is rotatable when turned by a key, wherein the rotor is mechanically coupled to the hook release spring to rotate the hook release spring to engage with the bag support hook and rotate the bag support hook to the reset position.

19. A bag hanger for supporting an intravenous (IV) bag, comprising:
a housing for holding internal components of the bag hanger; and
internal components of the bag hanger including at least one bag support hook having an extension portion extending from an interior of the housing and rotatable around an axle located within the housing, wherein the at least one bag support hook, in a reset position, provides support of the intravenous bag in a saddle portion of the at least one bag support hook up to a threshold weight limit, wherein the at least one bag support hook, in a triggered position initiated by a downward force in excess of the threshold weight limit rotating the bag support hook downward, rotates to a position in which the saddle portion of the at least one bag support hook is retracted within the housing, wherein the housing comprises a rear housing portion having a substantially circular first external profile along at least a top portion of the first external profile in a plane of a front edge of the rear housing portion, and a front housing portion having a second external profile matching the substantially circular first external profile of the rear housing portion along a back edge of the front housing portion, and wherein the front housing portion and the rear housing portion, when the front edge of the rear housing portion and the back edge of the front housing portion are joined, form a continuous surface having a third curved external profile in a direction perpendicular to the first external profile and the second external profile along the at least a top portion of the first external profile, whereby formation of a ligature around a top edge of the housing around the first external profile or the third external profile is prevented, and wherein the rear housing portion and the front housing portion define at least one slot extending along the first external profile and the second external profile at a junction between the rear housing portion and the front housing portion, through which the extension portion of the at least one bag support hook extends when the at least one bag support hook is in the reset position and through which the at least one bag support hook retracts when the at least one bag support hook is triggered.

20. A method of supporting an intravenous (IV) bag while preventing formation of a ligature, the method comprising:

mounting a housing of a bag hanger above a patient; and hanging an intravenous bag from a saddle portion of a bag support hook of the bag hanger when the bag support hook is in a reset position, wherein the bag support hook has an extension portion extending from an interior of the housing and that is rotatable around an axle located within the housing, and supports the intravenous bag up to a threshold weight limit; and initiating a triggered position of the bag support hook by applying a downward force on the saddle portion of the bag support hook in excess of the threshold weight limit, so that the bag support hook rotates downward to a position in which the bag support hook is released by retraction of the saddle portion of the bag support hook within the housing;

preventing formation of a ligature around a top edge of the housing and around sides of the housing by providing the housing having a rear housing portion with a substantially circular first external profile along at least a top portion of the first external profile in a plane of a front edge of the rear housing portion and a front housing portion having a second external profile matching the substantially circular first external profile of the rear housing portion along a back edge of the front housing portion, wherein the front housing portion and the rear housing portion, when the front edge of the rear housing portion and the back edge of the front housing portion are joined, form a continuous surface having a third curved external profile in a direction perpendicular to the first external profile and the second external profile along the at least a top portion of the first external profile, whereby securing a ligature around the first external profile or the third external profile is prevented, and wherein the rear housing portion and the front housing portion define a slot extending along the first external profile and the second external profile at a junction between the rear housing portion and the front housing portion, through which the extension portion of the bag support hook extends when the bag support hook is in the reset position and through which the bag support hook retracts when the bag support hook rotates to the triggered position.

* * * * *